United States Patent [19]

Helms et al.

[11] Patent Number: 4,947,127
[45] Date of Patent: Aug. 7, 1990

[54] MICROWAVE WATER CUT MONITOR

[75] Inventors: David A. Helms; Gregory J. Hatton; Michael G. Durrett, all of Houston; Earl L. Dowty, Katy; John D. Marrelli, Houston, all of Tex.

[73] Assignee: Texaco Inc., White Plains, N.Y.

[21] Appl. No.: 314,337

[22] Filed: Feb. 23, 1989

[51] Int. Cl.⁵ .............................................. G01R 27/02
[52] U.S. Cl. .................................. 324/640; 324/639; 73/61.1 R
[58] Field of Search .............. 324/58.5 A, 58.5 B, 324/58.5 R, 639, 640, 637; 73/61.1 R

[56] References Cited

U.S. PATENT DOCUMENTS

| | | | |
|---|---|---|---|
| 4,135,131 | 1/1979 | Larsen et al. | 324/58.5 A |
| 4,499,418 | 2/1985 | Helms et al. | 324/58.5 A |
| 4,651,085 | 3/1987 | Sakurai et al. | 324/58.5 A |
| 4,727,311 | 2/1988 | Walker | 324/58.5 A |
| 4,764,718 | 8/1988 | Revus et al. | 324/58.5 A |
| 4,767,982 | 8/1988 | Florig et al. | 324/58.5 A |

FOREIGN PATENT DOCUMENTS 1283632  1/1987  U.S.S.R. .................... 324/58.5 A

Primary Examiner—Reinhard J. Eisenzopf
Assistant Examiner—Maura K. Regan
Attorney, Agent, or Firm—Robert A. Kulason; James J. O'Loughlin; Ronald G. Gillespie

[57] ABSTRACT

A petroleum stream microwave water cut monitor includes test cell means which contains a reference petroleum multiphase fluid sample and which has a sample stream of a petroleum stream passing through it. A source transmits microwave energy to one of a first pair of antennae which irradiates the petroleum stream flowing in the test cell or the reference sample in the test cell with microwave energy. One of a second pair of antennae receives the microwave energy that has passed through either the petroleum stream or the reference sample. A detector detects the received microwave energy and provides a signal corresponding thereto. An indicator provides an indication of the water cut of the petroleum stream in accordance with the received signal power and a phase difference between the transmitted microwave energy and the received microwave energy.

6 Claims, 2 Drawing Sheets

MICROWAVE WATER CUT MONITOR

BACKGROUND OF THE INVENTION

Field of the Invention

The present invention relates to water cut monitors in general and, more particularly, to microwave water cut monitors.

SUMMARY OF THE INVENTION

A petroleum stream microwave water cut monitor includes test cell means which contains a reference petroleum multiphase fluid sample and which has a sample stream of a petroleum stream passing through it. A source transmits microwave energy to one of a first pair antennae which irradiates the petroleum stream flowing in the test cell or the reference sample in the test cell with microwave energy. One of a second pair of antennae receives the microwave energy that has passed through either the petroleum stream or the reference sample. A detector detects the received microwave energy and provides a signal corresponding thereto. An indicator provides an indication of the water cut of the petroleum stream in accordance with the received signal power and a phase difference between the transmitted microwave energy and the received microwave energy.

The objects and advantages of the invention will appear more fully hereinafter from a consideration of the detailed description which follows, taken together with the accompanying drawing wherein one embodiment of the invention is illustrated by way of example. It is to be expressly understood, however, that the drawings are for illustration purposes only and are not to be construed as defining the limits of the invention.

DESCRIPTION OF THE INVENTION

Figure 1:
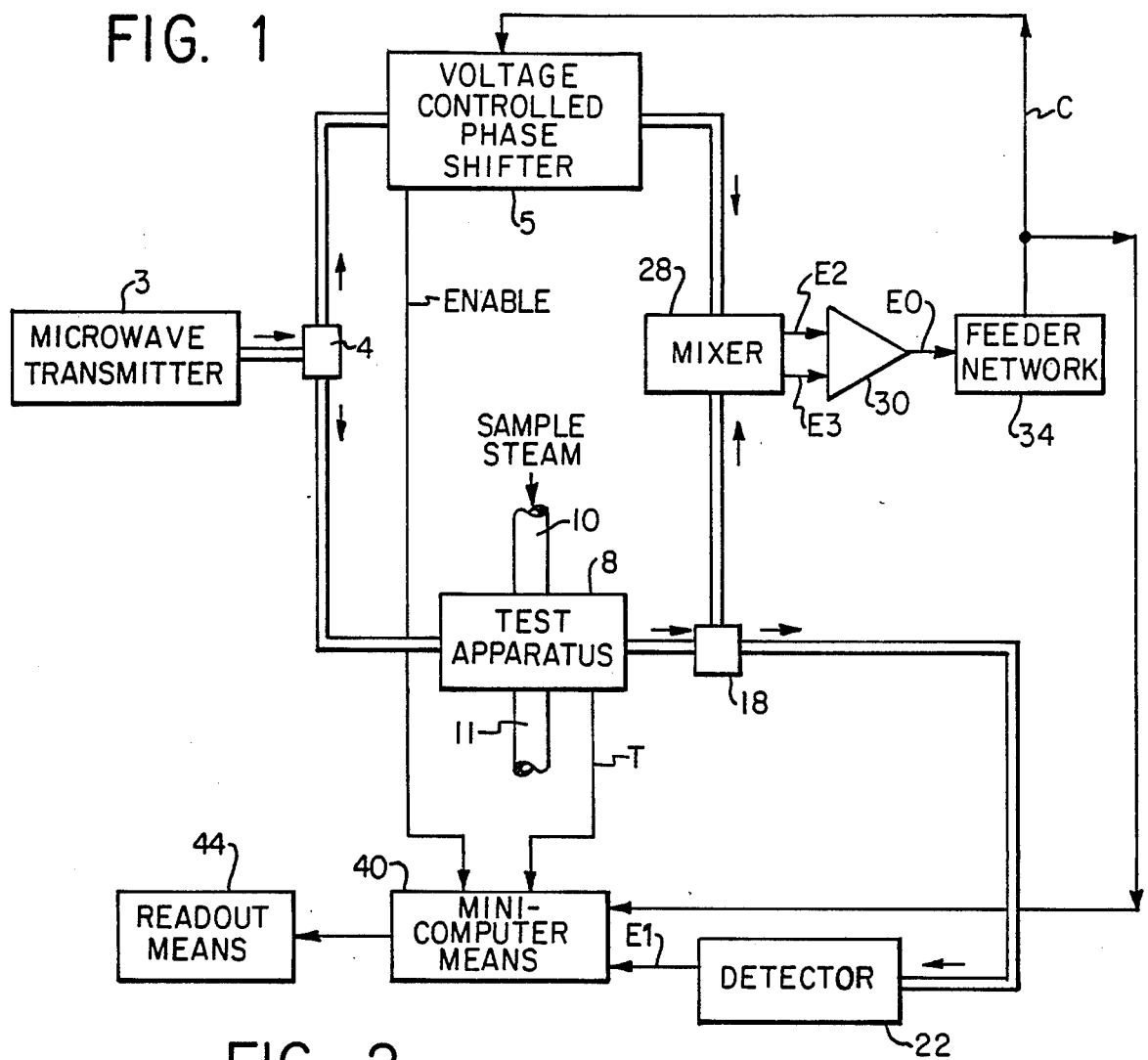
FIG. 1 is a partial simplified block diagram and a partial schematic of a microwave water cut monitor constructed in accordance with the present invention.

The water cut monitor shown in FIG. 1 includes a microwave transmitter 3 providing electromagnetic energy, hereinafter referred to as microwave energy, at a microwave frequency. Transmitter 3 is low powered and may use a microwave gun source. Transmitter 3 provides microwave energy to directional coupler 4. Directional coupler 4 provides microwave energy to a conventional type voltage controlled phase shifter 5 and to test apparatus 8. All conductance or carrying of microwave energy is accomplished by using conventional type waveguides and coaxial cables.

Test apparatus 8 has a line 10, carrying a sample stream of a multi-phase petroleum stream, entering apparatus 8. The sample stream leaves test apparatus 8 by way of a line 11. Apparatus 8 will be described in more detail hereinafter. Suffice to say at this point that microwave energy leaving test apparatus 8 in line 11, hereinafter referred to as test microwave energy, is microwave energy that is either passed through the sample stream or has passed through a reference sample. The test microwave energy is applied to a directional coupler 18. Directional coupler 18 provides the test microwave energy to a detector 22 and to a mixer 28. Detector 22 provides a signal E1 corresponding to the power of the microwave energy received by antenna 14.

Voltage control phase shifter 5 provides microwave energy, hereinafter called the reference microwave energy, to mixer 28 which mixes the reference microwave energy and the test microwave energy to provide two electrical signals E2, E3, representative of the phases of the reference microwave energy and the test microwave energy, respectively.

A differential amplifier 30 provides an output signal E0 in accordance with the difference between signals E2 and E3. Signal E0 is a function of the phase difference between the reference microwave energy and the test microwave energy and is provided to a feedback network 34. Feedback network 34 provides a signal C to voltage control phase shifter 5, controlling the phase of the reference microwave energy, and to a mini-computer means 40. Signal E0, and hence signal C, decreases in amplitude until there is substantially 90° phase difference between the reference microwave energy and the test microwave energy. Voltage control phase shifter 5 indicates the amount of phase shift required to eliminate the phase difference.

Signals E1, T and C are provided to a conventional type mini-computer means 40 which contains within it memory means having data related to phase and power for various percentages of water cuts that could be encountered in the production stream. Phase Shifter 5 also provides an enable signal to computer means 40 allowing computer means 40 to utilize signals T, C and E1 to select the proper water cut value computer means 40 provides signals, corresponding to the selected water cut value, to readout means 44 which may be either display means or record means or a combination of the two. It may we said that read out means 44, phase shifter 5, mini-computer means 40 in effect form indicator means With reference to FIGS. 1 and 2, test apparatus 8 includes a test cell 53. Test cell 53 will be described more fully hereinafter. Microwave energy from directional coupler 4 enters switch means 58 which provides microwave to test cell 53 through either a line 62 or a line 64. Line 62 provides the microwave to an antenna 63 which radiates the microwave energy into the sample stream. Similarly, when microwave energy is provided by line 64, it is provided to an antenna 65. Antenna 65 radiates the microwave energy into the reference sample. Line 66 carries test microwave energy received by an antenna 67 after it has passed through the sample stream. Similarly, line 69 carries microwave energy received by an antenna 70 after it has passed through the reference sample. Switch means 72 receives the test microwave energy from either line 66 or line 67 and provides it to directional coupler 18.

A reference sample source 77 provides the reference sample fluid to test cell 53 by way of a line 80 having a valve 84. A channel in test cell 53 connects line 80 to another line 88 having a valve 90. In operation, source 77 provides the reference fluid through test cell 53. A measurement could be made while it is flowing, or sample fluid could be contained in a static condition in test cell 53 by closing valve 90 until the channel within test cell 53 is completely filled. To drain the reference sample fluid from test cell 53 valve 84 is closed while valve 90 is opened.

Figure 3:
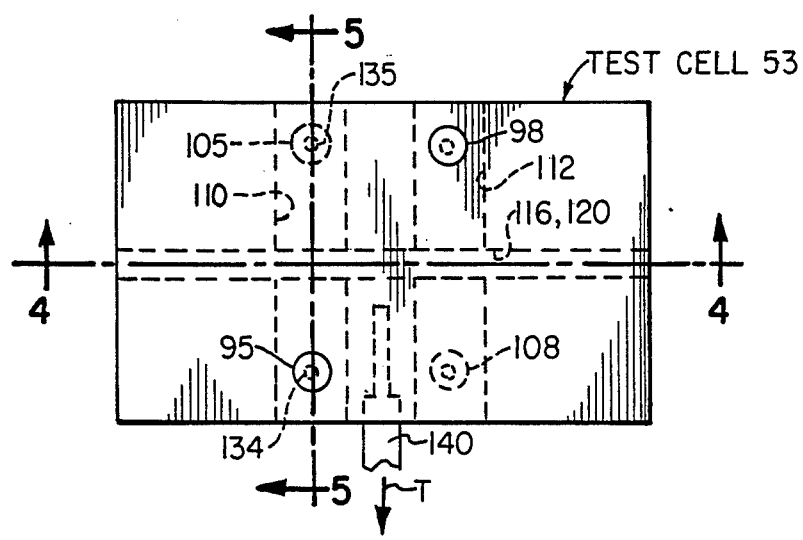
FIG. 3 is a drawing of the test cell shown in FIG. 2.

With reference to FIG. 3, there is shown test cell 53 having microwave entrance ports 95 and 98. On the other side of test cell 53 as represented by dash lines are microwave exit ports 105 and 108. Connecting microwave entrance port 95 and microwave exit port 105 is a microwave channel 110. Similarly a microwave channel 112 connects microwave entrance port 98 with microwave exit port 108.

Figure 4:
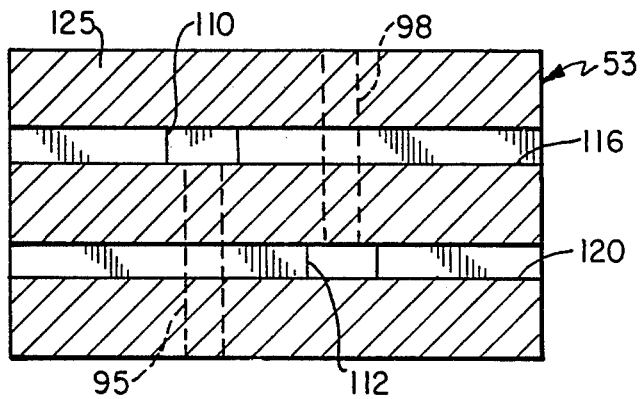
FIGS. 4 and 5 are cross-sectional drawings of the test cell shown in FIG. 3.

Also shown in FIG. 3 are fluid channels 116 and 120. Since fluid channels 116 and 120 are in line in this view of test cell 53 only one set of dash lines represents them. This can seen better in FIG. 4 which has a cut away view of test cell 53 in the direction of the arrows 4—4. There is shown a body 125 which may be made of metal having fluid channels 116 and 120 passing through it longitudinally and microwave channels 110 and 112 for the microwave energy cut transversely through it. It should be noted that channels 110 and 112 are shown as being offset from each other. However this offset is not necessary to the practice of the present invention.

It should also be noted that fluid channels 116, 120 have a rectangular cross-section so that the microwave energy that passes through the fluids, always has the same distance of passage.

Figure 5:
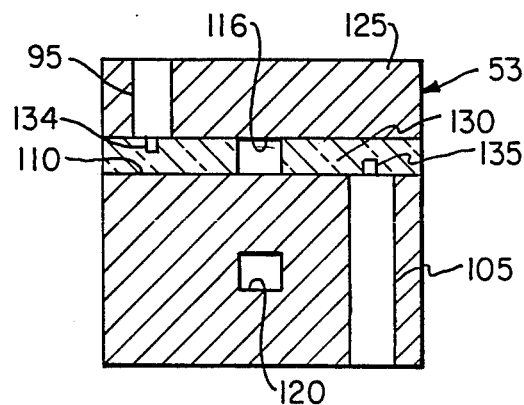

Referring to FIG. 5, there is a view of test cell 53 along the line BB in the direction of 5—5, shown in FIG. 3. Channel 110 is filled with a solid material 130, such as high density teflon, that is conductive to microwave energy, except for that portion of channel 110 that forms a cross-section of fluid channel 116 Cut into body 125 is microwave entrance port 95. Further there is another chamber 134 which connects microwave entrance port 95 and enters into material 130 in channel 110. This is for the insertion of microwave antenna 63, which may be of the commercial type made by Omni Spectra, Part No. 2057-5134-02, slightly modified for the present application. Similarly, microwave exit port 105, for antenna 67, is shown with an additional chamber 135 which enters into material 130. Again this is for the purpose of monitoring the sample stream. Basically it is the same type of antenna as is entered with entrance port 95, but again modified for the present application. The microwave energy when applied to the antenna 63 enters material 130 and is directed to cross channel 116 until it reaches the antenna 67 inserted in exit port 105.

Figure 2:
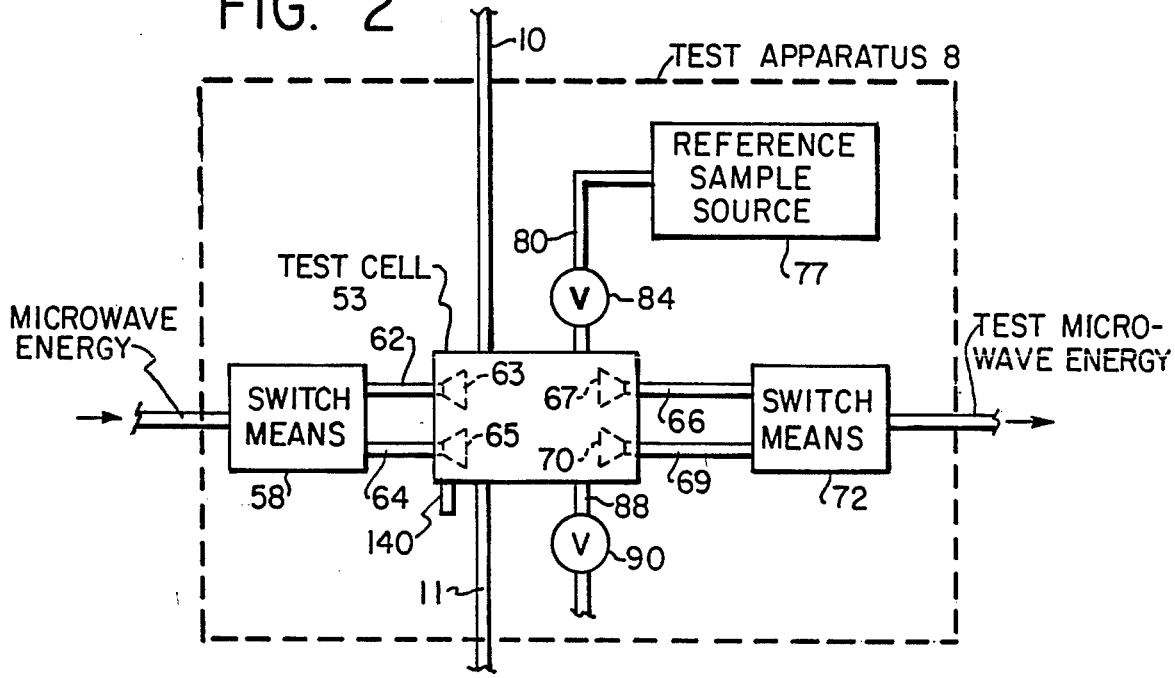
FIG. 2 is a simplified block diagram of the test apparatus shown in FIG. 1.

Referring also to FIG. 2, lines 10 and 11 are connected in the conventional manner to channel 110 so that the sample stream in line 10 will flow through test cell 53 to line 11. Similarly, lines 80 and 88 are connected to fluid channel 112 in such a manner that the sample fluid in line 80 will enter fluid channel 112 and exit test cell 53 through line 88. Similarly antenna 67 in entrance port 98 is connected to line 63 and antenna 70 in exit port 108 is connected to line 67.

As can be seen in FIG. 3, temperature sensor 140 which is a thermocouple, is inserted into a chamber cut into block 105 and thus reads the temperature of block 105 as the temperature of the reference and as of the production stream sample.

Basically, the reference sample's power and phase shift is used as base line data in mini-computer means 40. The base line data and the test data derived from the petroleum sample stream are temperature corrected by mini-computer means 40. Mini-computer means 40 determines the water-cut in accordance with the corrected base line data, the corrected test data and look-up table stored in its memory.

What is claimed is:

1. A petroleum stream microwave water cut monitor comprising:
   test cell means for containing a reference petroleum multiphase fluid sample and for having a sample stream of a petroleum stream flowing through it,
   source means for transmitting microwave energy,
   first antenna means connected to the source means for transmitting microwave energy into the petroleum sample stream or the reference sample,
   second antenna means for receiving microwave energy that has passed through the petroleum sample stream or the reference sample and providing the received microwave energy as test microwave energy,
   detector means connected to the second antenna means for detecting the power of the test microwave energy and providing a power signal corresponding thereto, and
   indicator means connected to the second antenna means, to the source means and to the detector means for providing an indication of the water cut of the petroleum stream in accordance with the power signal and the phase difference between the transmitted microwave energy and the received microwave energy.

2. A monitor as described in claim 1 further comprising:
   means for sensing the temperature of the reference sample and the sample stream and providing a temperature signal corresponding thereto, and
   wherein the indicator means provides the indication of the water cut in accordance with the power signal, the phase difference between the transmitted energy and the received microwave energy and the temperature signal.

3. A monitor as described in claim 2 in which the test cell means includes:
   a body having two channels therein for fluid passage and two channels for microwave energy passage,
   fluid source means for providing the reference sample to one of the fluid channels,
   means for receiving the sample stream and providing it to the other fluid channel,
   means for allowing the sample stream to exit from the body; and wherein the body has one fluid channel and one microwave channel intersecting each other at right angles and the other fluid channel and the other microwave channel intersecting each other at right angles.

4. A monitor as described in claim 3 in which each microwave channel contains a material, except for that portion of the microwave channel that crosses a fluid channel, that is impervious to fluids but permits passage of the microwave energy.

5. A monitor as described in claim 4 in which the first antenna means includes:
   first transmitter antenna means spatially arranged with one of the microwave channels for transmitting microwave energy into the one microwave channel,
   second transmitter antenna means spatially arranged with the other microwave channel for transmitting microwave energy into the other microwave channel, and
   first switch means connected to the source means and to the first and second transmitter antennas for providing the microwave energy transmitted by the source means to either the first transmitter antenna means or to the second transmitter antenna means; and the second antenna means includes:

a first receiving antenna spatially arranged with the one microwave channel, a second receiving antenna spatially arranged with the other microwave channel, second switching means connected to the first and second receiving antenna and cooperating with the first switching means for passing microwave energy that has passed through a fluid and received by a receiving antenna to the detector means and to the indicator means.

6. A monitor as described in claim 5 in which the solid material in the microwave channel is teflon.

* * * * *